United States Patent
Nakagami et al.

(10) Patent No.: US 6,217,910 B1
(45) Date of Patent: Apr. 17, 2001

(54) GRANULAR PREPARATION AND PRODUCING PROCESS THEREOF

(75) Inventors: Hiroaki Nakagami; Tadanao Yamao, both of Tokyo; Ario Funada, Shizuoka, all of (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/000,346
(22) PCT Filed: Jul. 19, 1996
(86) PCT No.: PCT/JP96/02028
  § 371 Date: Apr. 28, 1998
  § 102(e) Date: Apr. 28, 1998
(87) PCT Pub. No.: WO97/03656
  PCT Pub. Date: Feb. 6, 1997

(30) Foreign Application Priority Data

Jul. 21, 1995 (JP) .................................... 7-206726

(51) Int. Cl.⁷ ...................................................... A61K 9/32
(52) U.S. Cl. ........................... 424/497; 424/490; 424/489
(58) Field of Search ..................... 424/490, 489, 424/494, 486, 487, 497

(56) References Cited

U.S. PATENT DOCUMENTS 5,169,645  12/1992  Shukla et al. .
5,741,524  * 4/1998  Staniforth et al. ................... 424/489

FOREIGN PATENT DOCUMENTS

EP 0 263 083   4/1988  (EP) .
58-214333     12/1983  (JP) ................................ B01J/2/16
6-91150        4/1994  (JP) ................................ B01J/2/02
WO 94 12157    6/1994  (WO) .

OTHER PUBLICATIONS

International Search Report.

* cited by examiner

Primary Examiner—Thurman K. Page
Assistant Examiner—Blessing Fubara
(74) Attorney, Agent, or Firm—Sughrue, Mion, Zinn Macpeak & Seas, PLLC

(57) ABSTRACT

A granular preparation comprising particles prepared by melt granulation of a powdered low-melting oily substance and a powdered medicine, the particles being coated with a finely powdered hydrophobic and oil-absorbing high polymeric compound (if desired, together with a finely powdered diluent) by melt coating, and a producing process thereof. The preparation does not cake even under heat and humid conditions and is effective for masking bitterness of a medicine.

14 Claims, No Drawings

GRANULAR PREPARATION AND PRODUCING PROCESS THEREOF

TECHNICAL FIELD

This invention relates to a granular preparation which do not cake even under heat and humid conditions and in which an unpleasant taste of a medicine can be masked.

BACKGROUND ART

Among various known dosage forms such as tablets and capsules, granular preparations such as granules and powders have a great role to play. That is, a granular preparation is of great advantage in that a dose can be varied freely, it is easy to take for children and the aged, and compliance can be improved. In view of the fast expanding number of the aged patients in recent years, the demand for granular preparations has been increasing.

On the other hand, even granular preparation is not always easy to take when they contain a medicine having an unpleasant taste. Various pharmaceutical techniques have been proposed to solve this problem. The most frequently used technique is to coat the surface of particles with a coating agent which does not dissolve in the mouth, such as wax or water-insoluble polymers. The coating agent of this type has been applied by spray coating in the form of a solution in an organic solvent. However, use of an organic solvent involves many problems, such as adverse influence on workers' health, environmental pollution, and remaining solvent in the preparation. Hence, a method of using an aqueous coating composition prepared by dispersing a coating agent in water together with a plasticizer has been developed and used extensively. However, this method is still unsuitable for those substances which are unstable against water. Besides, where the method is applied to a medicine easily soluble in water, the medicine is easily dissolved in the coating composition. As a result, the particles tend to adhere to each other during coating to form agglomerates, or a coating layer cannot be formed sufficiently. Further, where the coating composition is applied by spray coating, there are so many variable manufacturing conditions, such as coating speed, temperature, and the like. Therefore, highly precise process control is required in order to obtain preparation with a constant quality.

Apart from the above-mentioned coating technique, a melt coating method has been proposed for the purpose of masking bitterness, in which a finely powdered medicine is melt-granulated together with glycerol monostearate, which is an oily substance, with or without a finely powdered diluent, and the resulting particles are prepared by melt coating with a coating agent consisting solely of talc. It has turned out, however, that the particles prepared by this method tend to cake with time when exposed to heat and humid conditions.

It is known that, in general, particles containing an oily substance cake when storaged at or below the melting point of the oily substance (see Wakiyama Naoki, *Pharm. Tech. Japan*, Vol. 10, p. 819 (1994)). It is reported said that such factors as the particle size and the oily substance content have influences on caking of the particles. As an approach to preventing granular preparations from agglomeration and caking, addition of a small amount of a finely powdered additive was proposed (see P. York, *J. Pharm. Sci.*, Vol. 64, pp. 1216–1221 (1975)), S. Dawoodbhai and C. T. Rhodes, *Drug Dev. Ind. Pharm.*, Vol. 16, pp. 2409–2429 (1990), and G. Gold, et al., *J. Pharm. Sci.*, Vol. 57, pp. 667–671 (1968)). It has been reported, however, that the addition of a small amount of a finely powdered additive to an oily substance-containing particle system induces a peculiar phenomenon that fluidity of the particles decreased, and further their caking increased (Wakiyama Naoki, ibid).

An object of the invention is to provide a granular preparations which does not cake even under heat and humid conditions and in which an unpleasant taste of a medicine can be masked.

DISCLOSURE OF INVENTION

The invention relates to a granular preparation comprising particles prepared by melt granulation of a powdered low-melting oily substance and a powdered medicine, the particles being coated with a finely powdered hydrophobic and oil-absorbing polymeric compound (if desired, together with a finely powdered diluent) by melt coating, and a producing process thereof.

The low-melting oily substance which can be used in the invention is not particularly limited as long as it is an oily substance having a melting point of 30 to 100° C., preferably 50 to 80° C. Examples of suitable low-melting oily substances include esters, such as glycerol monostearate, acetylated glycerol monostearate, sorbitan monostearate, hexadecyl palmitate, and octadecyl stearate; waxes, such as carnauba wax and bees wax; hydrocarbons, such as paraffin and microcrystalline wax; and fats and oils, such as hydrogenated oil, Japan wax, and cacao butter; with glycerol monostearate being preferred.

The low-melting oily substance having a particle size of 100 to 850 $\mu$m is usually used for preference, but a preferred particle size varies depending on the dosage form. For example, particles of 360 to 850 $\mu$m, preferably 350 to 700 $\mu$m, in a particle size are used for the preparation of granules; and particles of 100 to 250 $\mu$m, preferably 110 to 200 $\mu$m, in a particle size are used for the preparation of fine granules.

The terminology "particle size" as used herein except for Reference Examples and Examples is intended to mean an average particle size.

The low-melting oily substance is usually used in an amount of 0.01 to 0.5 part by weight, preferably 0.05 to 0.3 part by weight, per part by weight of the finally obtained granular preparation.

While the medicine for use in the present invention is not particularly limited, those having bitterness, such as Nefilacetam, Levofloxacin, Ecabapide, etc., are preferred to the object and effect of the present invention.

The medicine is used in a powdered form having a particle size of not greater than 50 $\mu$m, preferably several to 10 $\mu$m. The medicine is usually used in an amount of 0.01 to 0.5 part by weight per part by weight of the finally obtained granular preparation. When the medicine and the low-melting oily substance are granulated by a method of melt granulation, powdered diluents such as corn starch, lactose, and talc may be used in combination, if desired. In general, diluents having a particle size of not greater than 50 $\mu$m are used in an amount of about 0.02 to 0.3 part by weight per part by weight of the finally obtained granular preparation.

The terminology "melt granulation" as used herein is intended to mean a method in which mononuclear particles are prepared by adhering uniformly the powdered medicine (and the diluent if used) to the oily substance as a core with using the resulting stickness from heat melting of the oily substance in a fluidized bed system (see *Ryushi Sekkei to Seizai Gijutsu*, pp. 130–132, Yakugyo Jihosha (Oct. 30, 1994)). More specifically, melt granulation is carried out by mixing a finely powdered low-melting oily substance, a powdered medicine, and, if desired, a powdered diluent, agitating the mixed powder to make a fluidized powder bed while heating to a temperature at or above the melting point of the low-melting oily substance, followed by cooling to uniformly adhere the medicine and the diluent around the low-melting oily substance as a core, and cooling below the melting point to obtain mononuclear particles.

The heating temperature for melt granulation is usually about 5 to 45° C. higher than the melting point of the low-melting oily substance. The granulation time, though varying depending on the raw materials used and the scale of production, is usually 10 to 30 minutes in a production scale of about 1 to 10 kg.

The resulting particles are then coated with a coating agent comprising a finely powdered hydrophobic and oil-absorbing polymeric compound and, if desired, fine powder of a diluent such as talc, by melt coating to obtain the granular preparation of the invention.

The term "hydrophobic" as used for the polymeric compound is intended to mean "being compatible with oil more than with water". Substances with such properties are almost insoluble in water but are easily soluble in oil or nonpolar solvents. The term "oil-absorbing" as used here means properties of absorbing oil selectively and swelling with oil.

Cellulose derivatives, such as ethyl cellulose, are included in the hydrophobic and oil-absorbing polymeric compounds. Those having a particle size of not greater than 10 $\mu$m are usually used. The hydrophobic and oil-absorbing polymeric compound is used in an amount of about 0.0001 to 0.5 part by weight, preferably 0.001 to 0.1 part by weight, per part by weight of the resulting granular preparation.

The diluent which may be used in melt coating usually has a particle size of not greater than 50 $\mu$m and is used in an adequate amount, usually about 0.1 to 0.5 part by weight per part by weight of the resulting granular preparation.

The terminology "melt coating" as used in the invention means a technique comprising mixing the particles prepared by melt granulation with a finely powdered coating agent and heating the mixed powder in a fluidized bed system at or above the melting point of the low-melting oily substance, thereby to make the low-melting oily substance melt and bleed on the surface of the particles and to adhere the coating agent around the particles with using the stickiness of the molten oily substance (see *Ryushi Sekkei to Seizai Gijutsu*, pp. 132–134, Yakugyo Jihosha (Oct. 30, 1994)).

Melt coating in the invention can be carried out by mixing the particles prepared by melt granulation as described above with a finely powdered hydrophobic and oil-absorbing polymeric compound and, if desired, a finely powdered diluent, heating the mixed powder at or above the melting point of the low-melting oily substance while fluidizing, tumbling or agitating thereby to adhere the polymeric compound around the particles to form a coating layer comprising the low-melting oily substance, the polymeric compound and, if used, the diluent.

Sufficient effects of melt coating can be expected by using the heating conditions and the granulation time similar to those employed in the melt granulation.

Cooling after melt coating gives a granular preparation as an objective product.

The powdered materials used in the invention, i.e., the powdered low-melting oily substance, the powdered medicine, the powdered diluent, and the powdered polymeric compound, are prepared by grinding the raw material by means of a generally employed pulverizer, such as a ball mill or a jet mill, and sieving the powder to obtain particles of desired size, if necessary.

The particle size of the prepared granular preparation can be made more uniform by passing through a sieve of desired mesh.

Mixing of the resulting granular preparation with an appropriate glidant and/or a coating agent can provide a granular preparation having a greater effect on preventing of caking. Usable glidants include talc, silicic acid anhydride, magnesium aluminometasilicate, a mixture thereof and the like. Usable coating agents include, titanium oxide, magnesium oxide, a mixture thereof and the like. The glidant and/or coating agent are usually used in an amount of 1 to 5% by weight based on the total weight of thus prepared granular preparation. The particle size of the glidant agent or the coating agent is in accordance with the standard of commercially available glidant agents or coating agent, and such size is usually in the rage of 0.001 to 75 $\mu$m in the form of a particle size.

BEST MODE FOR CARRYING OUT INVENTION

The present invention will now be illustrated in greater detail with reference to Reference Examples and Examples.

REFERENCE EXAMPLE 1

Into a fluidized bed granulator (Gllat WSG-5) were put 1.2 kg of Nefilacetam (average particle size: 50 $\mu$m or less), 1.08 kg of talc (particle size: 100 $\mu$m or less), 0.534 kg of lactose (particle size: 250 $\mu$m or less), 0.27 kg of corn starch (particle size: 125 $\mu$m or less), and 0.846 kg of glycerol monostearate (average particle size: 100 to 200 $\mu$m), and the mixed powder was fluidized under heating at an inlet air temperature of 90° C. to granulate. After cooling, the particles were passed through a sieve having an opening size of 500 $\mu$m to obtain particles (fine granules).

The resulting particles weighing 3.275 kg were put in a fluidized bed granulator together with 1.650 kg of talc (particle size: 100 $\mu$m or less) and fluidized while heating at an inlet air temperature of 90° C. for about 20 minutes until all the talc powder adhered to the particles. The hot air was displaced with room air by operating the damper to cool the coated particles to 40° C. to obtain a granular preparation (fine granules).

EXAMPLE 1

The particles obtained by melt granulation before melt coating in Reference Example 1 were subjected to melt coating in the same manner as in Reference Example 1 except for replacing part of the talc powder with ethyl cellulose (average partivle size: 10 $\mu$m or less) in an amount of 2 to 50% by weight based on the total coating agent to obtain a granular preparation (fine granules).

Each of the granular preparations prepared in Reference Example 1 and Example 1 were evaluated in terms of caking, masking in the mouth, and resolution (T75%) in accordance with the following test methods. The caking was observed with the naked eye (Table 1).

In Table 1, "+" is caking, "±" is partial caking, and "−" is no caking.

TABLE 1

Effect of Ethyl Cellulose on Prevention
of Caking of Nephilacetum Fine Granules (1 month)

| | Reference Example 1 | Example 1A | Example 1B | Example 1C | Example 1D | Example 1E |
|---|---|---|---|---|---|---|
| Ethyl Cellulose Content (wt %) | 0 | 2 | 5 | 10 | 20 | 50 |
| 25° C., 75%* | – | – | – | – | – | – |
| 30° C., 92%* | ± | – | – | – | – | – |
| 40° C., 75%* | + | – | – | – | – | – |
| 50° C. | + | – | – | – | – | – |

"*": humidity

It is seen from Table 1 that ethyl cellulose exhibits a preventive effect on caking irrespective of its content in the coating agent.

A sample preparation weighing 0.75 g was kept in the month, and the time until bitterness was felt was measured to obtain an average (n=6) (in the table, the figures in the parentheses are the minimum and the maximum in each run). A resolution test was conducted according to Japanese Pharmacopoeia, General Test Methods, Resolution Test Method (2). Water was used as a test fluid. An aliquot of the test fluid was taken after 2, 5, 10, 15, 20, 30, 40 and 60 minutes from the start of the test, and the absorbance was measured to obtain the rate of resolution of Nefilacetam. The time required for the rate of resolution reached 75% (T75%) was calculated (Table 2).

TABLE 2

Masking Time and Resolution Time (T75%)
of Nefilacetam Fine Granules

| | Reference Example 1 | Example 1A | Example 1B | Example 1C | Example 1D | Example 1E |
|---|---|---|---|---|---|---|
| Ethyl Cellulose Content (wt %) | 0 | 2 | 5 | 10 | 20 | 50 |
| Masking Time (sec) | 20 (15–24) | 25.1 (19–31) | 27.5 (20–36) | 29.6 (20–38) | 28.0 (18–35) | 27.5 (15–35) |
| Elution Time (min) (T75%) | 7.2 | 7.5 | 7.7 | 8.9 | 13.0 | 13.2 |

As is shown in Table 2, the masking time gradually increases with an increase in ethyl cellulose content. As for the resolution time (T75%), the change is very small with the ethyl cellulose content increasing up to 10%, while showing an increasing tendency with the ethyl cellulose content increasing over 10%.

EXAMPLE 2

The granular preparation obtained in Example 1A weighing 988 g was thoroughly mixed with 12 g of a 9:1 (by weight) mixture of talc and silicic anhydride to prepare a preparation containing a fluidizing agent.

REFERENCE EXAMPLE 2

Into a fluidized bed granulator (FLO-5 type) were put 0.6 kg of Levofloxacin (average particle size: 20 μm or less), 1.5 kg of talc, 1.176 kg of lactose, and 0.924 kg of glycerol monostearate (average particle size: 100 to 200 μm), and the mixed powder was fluidized under heating at an inlet air temperature of 90° C. to granulate. After cooling, the particles were passed through a sieve having an opening size of 500 μm to obtain granules (fine granules).

The resulting granules weighing 3.5 kg were put into a fluidized bed granulator together with 1.5 kg of talc and fluidized while heating at an inlet air temperature of 90° C. for about 15 minutes until all the talc powder adhered to the particles. The hot air was displaced with room air by operating the damper to cool the coated particles to 40° C. to obtain a granular preparation (fine granules).

The respective particle sizes of the talc and lactose used above were same as used in Reference Example 1.

EXAMPLE 3

The particles obtained by melt granulation before melt coating in Reference Example 2 were subjected to melt coating in the same manner as in Reference Example 2 except for replacing part of the talc powder with ethyl cellulose (average particle size: 10 μm or less) in an amount of 11.7% by weight, based on the total coating agent to obtain a granular preparation (fine granules).

Each of the granular preparations prepared in Reference Example 2 and Example 3 was evaluated in terms of masking in the mouth and resolution (T75%) in the same manner as described above. Table 3 shows the minimum and the maximum masking time until bitterness is felt and also shows the time required for the rate of resolution reached 75% (Table 3).

TABLE 3

Masking Time and Elution Time (T75%) of Levofloxacin Fine Granules

|  | Reference Example 2 | Example 3 |
|---|---|---|
| Ethyl Cellulose Content (wt %) | 0 | 11.7 |
| Masking Time (sec) | 20–40 | 30–50 |
| Resolution Time (min) (T75%) | 4.3 | 7.4 |

EXAMPLE 4

The granular preparation obtained in Example 3 weighing 967 g was mixed with 33 g of a 10:1 (by weight) mixture of silicic anhydride and talc (average particle size of the mixture: 50 μm or less) to prepare a preparation containing a glidant. The resulting preparation was sealed in a bottle.

The resulting preparations sealed in a bottle were evaluated in terms of caking in accordance with the following test method.

Caking test

Twenty grams of the resulting sample was sealed in a bottle standardized as No. 5, kept under the conditions shown in Table 4 below, and cooled to room temperature (one hour at room temperature). The results obtained are shown in Table 4 below, in which:

+: caking . . . whole or partial amount of tested sample was remaining in the bottle even after the bottle was turned upside down.

±: partially caking . . . no remaining test sample in the bottle, however, some agglomerates were absorbed in the dropped sample after the bottle was turned upside down.

−: no caking . . . no remaining test sample in the bottle and no agglomerates in the dropped sample after the bottle was turned upside down.

TABLE 4

Caking of Levofloxacin Fine Granules

|  | Reference Example 2 | Example 4 |
|---|---|---|
| Ethyl Cellulose Content (wt %) | 0 | 11.7 |
| 40° C. × 1 month | + | − |
| 50° C. × 2 weeks | + | − |
| 60° C. × 1 week | + | − |

EXAMPLE 5

The granular preparation obtained in Example 3 weighing 959.5 g was mixed with 40.5 g of a 20.5:20 (by weight) mixture of titanium oxide and silicic anhydride (average particle size of the mixture: 50 μm or less) to prepare a preparation containing a glidant and a coating agent. The obtained preparation was sealed in a bottle and kept under the conditions shown in Table 5 below. The caking of the preparation was evaluated. The results are shown in Table 5 below.

TABLE 5

| Conditions | Example 5 |
|---|---|
| 40° C. × 2 months | − |
| 50° C. × 2 months | − |
| 60° C. × 1 week | − |

EXAMPLE 6

Into a fluidized bed granulator (FLO-5 type) were put 1.2 kg of Nefilacetam (average particle size: 50 μm or less), 0.87 kg of talc, 0.534 kg of lactose, 0.27 kg of corn starch (particle size: 125 μm or less), 0.846 kg of glycerol monostearate (average particle size: 100 to 200 μm) and 0.12 kg of croscarmellose sodium (particle size: 250 μm or less), and the mixed powder was fluidized under at an inlet air temperature of 90° C. to granulate. After cooling, the particles were passed through a sieve having an opening size of 500 μm to obtain particles (fine granules).

The resulting particles weighing 3.2 kg were put in a fluidized bed granulator together with 1.65 kg of talc and 0.035 kg of ethyl cellulose (average particle size: 10 μm or less) and fluidized while heating at an inlet air temperature of 90° C. for about 20 minutes until all the talc and ethyl cellulose adhered to the particles.

The hot air was displaced with room air by operating the damper to cool the coated particles to 40° C. to obtain a granular preparation (fine granules).

Thus obtained granular preparation weighing 980 g was mixed with 20 g of a 15:5 (by weight) mixture of titanium oxide and silicic anhydride (average particle size of the mixture: 50 μm or less) to prepare a preparation containing a glidant and a coating agent. Twenty grams of the resulting preparation was sealed in a bottle standardized as No. 5, kept under the conditions shown in Table 4 below. The respective particle sizes of the talc and lactose used above were same as used in Reference Example 1.

The caking of the preparation was evaluated in the same manner as in Example 4. The results are shown in Table 6 below.

TABLE 6

Caking of Nefilacetam Fine Granules

| Condition | Example 6 |
|---|---|
| 40° C. × 75%* × 1 month | − |
| 30° C. × 92%* × 1 month | − |
| 50° C. × 2 months | − |
| 60° C. × 1 week | − |

INDUSTRIAL APPLICABILITY

As described above, the granular preparation of the present invention exhibits excellent properties with respect to preventing of caking, masking of the unpleasant taste of a medicine in the mouth, release of the medicine, appearance, hardness, stability, and the like. Additionally, the present invention is advantageous in that:

(1)

Unlike the conventional masking particles, there is no need of separately preparing a binding solution or a coating composition. Therefore, the production time can be greatly shortened, and granular preparation of constant quality can be produced in good yield by the use of a simple apparatus without requiring strict and complicated manufacturing conditions.

(2)

No solvent is used. Therefore, the problems arising from the use of an organic solvent are not involved in terms of safety, hygiene, environmental pollution, and remaining of a solvent in the product. The stability of the medicine is not impaired.

(3)

The particle size of the product can easily be controlled by varying the particle size of the low-melting oily substance. For example, in using glycerol monostearate having an average particle size of 150 to 250 μm in melt granulation, fine granules having a particle size of 250 to 500 μm is obtained; in using glycerol monostearate having an average particle size of 300 to 850 μm, granules having a particle size of 500 to 1400 μm are obtained.

(4)

The masking properties and the release of the medicine can be controlled by adjusting the amount of the low-melting oily substance or the hydrophobic and oil-absorbing high polymeric compound or the kind or amount of the diluent.

What is claimed is:

1. A granular preparation comprising core granular particles prepared by melt granulation of a powdered low-melting oily substance and a powdered medicine, and melt coating the core granular particles with a finely powdered hydrophobic and oil-absorbing polymeric compound.

2. A process for producing a core granular particle preparation comprising melt granulating a powdered low-melting oily substance and a powdered medicine and coating the resulting core granular particles with a finely powdered hydrophobic and oil-absorbing high polymeric compound by melt coating.

3. A granular preparation as claimed in claim 1, wherein said low-melting oily substance is a fat or an oil.

4. A granular preparation as claimed in claim 3, wherein said fat or oil is glycerol monostearate.

5. A granular preparation as claimed in claim 1, wherein said hydrophobic and oil-absorbing polymeric compound is ethyl cellulose.

6. A granular preparation as claimed in any of claims 3, 4 and 5, wherein said medicine is Nefilacetam.

7. A granular preparation as claimed in any of claims 3, 4 and 5, wherein said medicine is Levofloxacin.

8. A granular preparation as claimed in any of claims 1, 3, 4, and 5, wherein said low-melting oily substance has an average particle size of 100 to 850 μm.

9. A granular preparation as claimed in claim 8, wherein said medicine has an average particle size of not greater than 50 μm.

10. A mixture comprising;
   a granular preparation comprising core granular particles prepared by melt granulation of a powdered low-melting oily substance and a powdered medicine, the core granular particles being coated with a finely powdered hydrophobic and oil-absorbing polymeric compound by melt coating; and
   a glidant and/or a coating agent.

11. A mixture as claimed in claim 10, wherein said medicine is Nefilacetam, said low-melting oily substance is glycerol monostearate, said hydrophobic and oil-absorbing polymeric compound is ethyl cellulose, said glidant is silicic acid anhydride and said coating agent is titanium oxide.

12. A mixture as claimed in claim 10, wherein said medicine is Levofloxacin, said low-melting oily substance is glycerol monostearate, said hydrophobic and oil-absorbing polymeric compound is ethyl cellulose, said glidant is silicic acid anhydride and said coating agent is titanium oxide.

13. A granular preparation according to claim 6, wherein said low-melting oily substance has an average particle size of 100 to 850 μm.

14. A granular preparation according to claim 7, wherein said low-melting oily substance has an average particle size of 100 to 850 μm.

* * * * *